United States Patent
Pellicciari et al.

(10) Patent No.: US 10,815,267 B2
(45) Date of Patent: Oct. 27, 2020

(54) 3-DESOXY DERIVATIVE AND PHARMACEUTICAL COMPOSITIONS THEREOF

(71) Applicant: Intercept Pharmaceuticals, Inc., New York, NY (US)

(72) Inventors: Roberto Pellicciari, Perugia (IT); Antimo Gioiello, Perugia (IT)

(73) Assignee: Intercept Pharmaceuticals, Inc., New York, NY (US)

( * ) Notice: Subject to any disclaimer, the term of this patent is extended or adjusted under 35 U.S.C. 154(b) by 0 days.

(21) Appl. No.: 15/451,818

(22) Filed: Mar. 7, 2017

(65) Prior Publication Data

US 2017/0260225 A1  Sep. 14, 2017

Related U.S. Application Data

(60) Provisional application No. 62/306,914, filed on Mar. 11, 2016.

(51) Int. Cl.
| | |
|---|---|
| *C07J 11/00* | (2006.01) |
| *A61K 47/54* | (2017.01) |
| *C07J 9/00* | (2006.01) |
| *C07J 31/00* | (2006.01) |

(52) U.S. Cl.
CPC ............ *C07J 11/00* (2013.01); *A61K 47/542* (2017.08); *C07J 9/005* (2013.01); *C07J 31/006* (2013.01)

(58) Field of Classification Search
CPC ........... C07J 11/00; C07J 9/005; C07J 31/006
USPC ........................................ 552/553, 610, 612
See application file for complete search history.

(56) References Cited

U.S. PATENT DOCUMENTS

| | | | |
|---|---|---|---|
| 9,611,289 B2 * | 4/2017 | Pellicciari | C07J 9/005 |
| 2013/0261317 A1 | 10/2013 | Moriarty et al. | |
| 2014/0371190 A1 * | 12/2014 | Pellicciari | C07J 9/005 |
| | | | 514/182 |
| 2019/0002496 A1 | 1/2019 | Pellicciari | |

FOREIGN PATENT DOCUMENTS

| | | | |
|---|---|---|---|
| WO | WO 2014/184271 A1 | 11/2014 | |
| WO | WO 2015/181275 A1 | 12/2015 | |
| WO | WO 2017/027396 A1 | 2/2017 | |

OTHER PUBLICATIONS

Ali; Annals of Translational Medicine; 2015, 3(1):5, 1-16.*
Bidstrup, et al. "CYP2C8 and CYP3A4 are the principal enzymes involved in the human in vitro biotransformation of the insulin secretagogue repaglinide", *Br. J. Clin. Pharmacol.*, 2003, 56, p. 305-314.
Crawley, "Farnesoid X receptor modulators: a patent review", *Expert Opinion on Therapeutic Patents*, 2010, 20, p. 1047-1057.
Cree et al. "Measurement of Cytotoxicity by ATP-based Luminescence Assay in Primary Cell Cultures and Cell Lines", *Toxicology In Vitro*, 1997, 11, p. 553-556.
Crouch et al., "The use of ATP bioluminescence as a measure of cell proliferation and cytotoxicity", *Journal of Immunological Methods*, 1993, 160, p. 81-88.
Dorn et al. "Evaluation of a High-Throughput Fluorescence Assay Method for hERG Potassium Channel Inhibition", *Journal of Biomolecular Screening*, 2005 10, 4, p. 339-347.
Heery et al., "Asignaturemotif in transcriptional co-activators mediates binding to nuclear receptors", *Nature*, 1997, 387, p. 733-736.
Kangas et al. "Bioluminescence of Cellular ATP: A New Method for Evaluating Cytotoxic Agents in vitro", *Medical Biology*, 1984, 62, p. 338-343.
Kawamata et al., "A G Protein-coupled Receptor Responsive to Bile Acids", *J. Biol. Chem.*, 2003, 278, p. 9435-9440.
Makishima et al., "Identification of a Nuclear Receptor for Bile Acids", *Science*, 1999, 284, p. 1362-1365.
Maruyama et al., "Identification of membrane-type receptor for bile acids (M-BAR)", *Biochemical and Biophysical Research Communications*, 2002, 298, p. 714-719.
Nolte et al. "Ligand binding and co-activator assembly of the peroxisome proliferator-activated receptor-γ", *Nature*, 1998, 395, p. 137-143.
Obach et al. "The Utility of in Vitro Cytochrome P450 Inhibition Data in the Prediction of Drug-Drug Interactions", *The Journal of Pharmacology and Experimental Therapeutics*, 2006, 316, p. 336-348.

(Continued)

*Primary Examiner* — Pancham Bakshi
(74) *Attorney, Agent, or Firm* — Cooley LLP; Ivor R. Elrifi; Chen Chen

(57) ABSTRACT

The present application provides Compound 1:

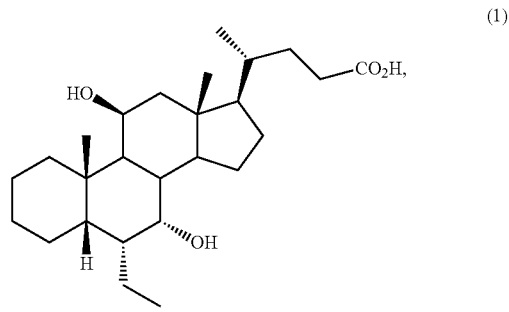

(1)

or a pharmaceutically acceptable salt or amino acid conjugate thereof. The present invention relates to an FXR activator and to methods of making and using said compound.

4 Claims, 1 Drawing Sheet

(56) References Cited

OTHER PUBLICATIONS

Onate et al. "Sequence and Characterization of a Coactivator for the Steroid Hormone Receptor Superfamily", *Science,* 1995, 270, p. 1354-1357.
Parks, et al. "Bile Acids: Natural Ligands for an Orphan Nuclear Receptor", *Science,* 1999, 284, p. 1365-1368.
Petty et al., "Comparison of MTT and ATP-Based Assays for the Measurement of Viable Cell Number", *J. Biolumin. Chemilumin.* 1995, 10, p. 29-34.
Storer et al. "Revalidation of the in vitro alkaline elution/rat hepatocyte assay for DNA damage: improved criteria for assessment of cytotoxicity and genotoxicity and results for 81 compounds", *Mutation Research,* 1996, 368, p. 59-101.
Torchia et al. "The transcriptional co-activator p/CIP binds CBP and mediates nuclear-receptor function", *Nature,* 1997, 387, p. 677-684.
Wang et al. "SRC-1 and GRIP1 Coactivate Transcription with Hepatocyte Nuclear Factor 4", *J. Biol. Chem.,* 1998, 273, p. 30847-30850.
Zhu et al. "Cloning and Identification of Mouse Steroid Receptor Coactivator-1 (mSRC-1), as a Coactivator of Peroxisome Proliferator-Activated Receptor $\gamma$", *Gene Expression,* 1996, 6, p. 185-195.

\* cited by examiner

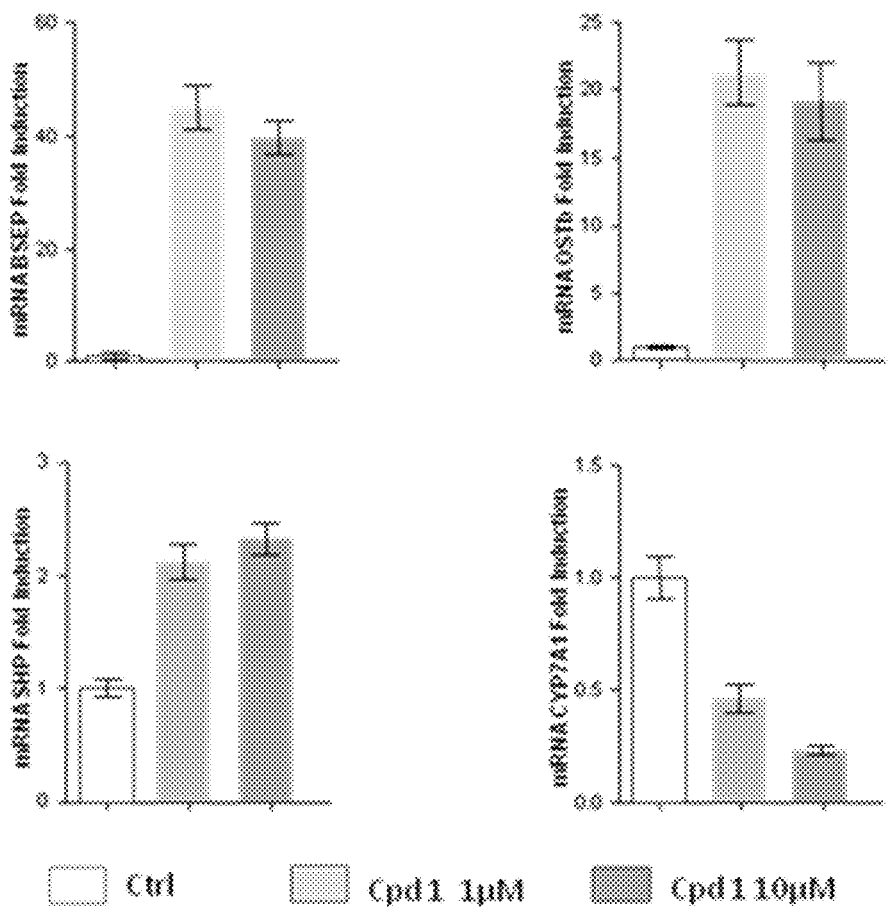

3-DESOXY DERIVATIVE AND PHARMACEUTICAL COMPOSITIONS THEREOF

BACKGROUND

Liver disorders occur widely in the population and are a risk factor for early mortality. For example, non-alcoholic fatty liver disease (NAFLD) is a disorder affecting millions of adults in the United States, and refers to conditions where there is an accumulation of excess fat in the liver of people who drink little or no alcohol. The most common form of NAFLD is a non-serious condition called hepatic steatosis (fatty liver), in which fat accumulates in the liver cells. NAFLD most often presents itself in individuals with a constellation of risk factors called metabolic syndrome, which is characterized by elevated fasting plasma glucose with or without intolerance to post-prandial glucose, being overweight or obese, high blood lipids such as cholesterol and triglycerides and low high-density lipoprotein cholesterol levels, and high blood pressure; but not all patients have all the manifestations of metabolic syndrome. Obesity is thought to be the most common cause of NAFLD and some experts estimate that about two-thirds of obese adults and one-half of obese children may have fatty liver.

People with NAFLD may develop a more serious condition called non-alcoholic steatohepatitis (NASH). About two to five percent of adult Americans and up to 20% of those who are obese may suffer from NASH. In NASH, fat accumulation in the liver is associated with inflammation and different degrees of scarring. NASH is a potentially serious condition that carries a substantial risk of progression to end-stage liver disease, cirrhosis and hepatocellular carcinoma. Some patients who develop cirrhosis are at risk of liver failure and may eventually require a liver transplant. NASH is a leading cause of end-stage liver disease while NAFLD, and to an even greater degree NASH, are intimately related to states of metabolic syndrome, including insulin resistance and type 2 diabetes mellitus, and abdominal obesity.

There are no drugs currently approved to prevent or treat NAFLD or NASH. A number of pharmacological interventions have been tried but with overall limited benefit. Antioxidant agents may arrest lipid peroxidation and cytoprotective agents stabilize phospholipid membranes, but agents tried unsuccessfully or with only modest benefit so far include ursodeoxycholic acid, vitamins E and C, and pentoxifylline, amongst others. Weight-loss agents such as Orlistat have had no significant benefit compared to just the use of diet and exercise to achieve weight loss alone. Most weight-loss studies in NAFLD/NASH have been pilot studies of short duration and limited success, reporting only a modest improvement in necroinflammation or fibrosis. Moreover, an investigational new drug encounters a variety of obstacles that may prevent its further development. Such obstacles may include poor tissue distribution, a non-suitable pharmacokinetic profile, safety issues such as toxicity, and/or undesirable drug-drug interactions. Despite ongoing efforts, there remains a significant unmet clinical need for an effective and well-tolerated compound that can treat or slow down the progression of NAFLD and NASH.

The present invention addresses these needs. Therefore, it is the object of the present invention to provide a novel therapeutic agent to treat liver disorders such as NAFLD and NASH while exhibiting physicochemical, in vitro and/or in vivo ADME (adsorption, distribution, metabolism and excretion) properties superior to known compounds and/or superior pharmacokinetics in vivo.

SUMMARY

An objective of the present invention is to provide a compound that activates the Farnesoid X receptor (FXR) and is therefore useful to treat FXR related disorders including NAFLD and NASH. Accordingly, the present invention provides Compound 1:

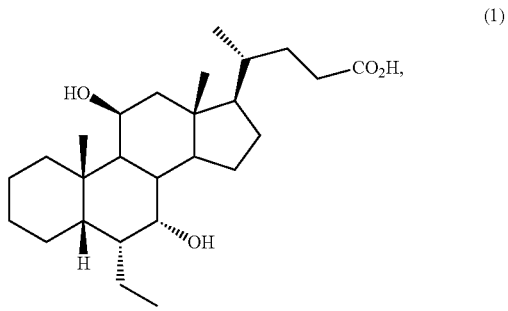 [SMILES: CC[C@H]1[C@@H](O)C2C3CC[C@H]([C@H](C)CCC(=O)O)[C@@]3(C)C[C@H](O)C2[C@@]2(C)CCCC[C@@H]12]

(1)

or a pharmaceutically acceptable salt or amino acid conjugate thereof.

The present invention further provides a pharmaceutical composition comprising Compound 1 or a pharmaceutically acceptable salt or amino acid conjugate thereof, and a pharmaceutically acceptable carrier or excipient.

The present invention also provides a method for treating or preventing a disease or condition activated by FXR, comprising administering to a subject in need thereof an effective amount of Compound 1 or a pharmaceutically acceptable salt or amino acid conjugate thereof.

The present invention also provides for the manufacture of a medicament for treating or preventing a disease or condition activated by FXR, wherein the medicament comprises Compound 1 or a pharmaceutically acceptable salt or amino acid conjugate thereof.

The present invention further provides compositions, including pharmaceutical compositions, for use in treating or preventing a disease or condition activated by FXR, wherein the composition comprises Compound 1 or a pharmaceutically acceptable salt or amino acid conjugate thereof.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. The materials, methods, and examples are illustrative only and are not intended to be limiting. Other features and advantages of the invention will be apparent from the following detailed description.

BRIEF DESCRIPTION OF THE FIGURES

FIG. 1 shows the expression levels of FXR Target Gene Panel.

DETAILED DESCRIPTION

The present invention is based on the discovery that Compound 1 is a potent and selective activator of the Farnesoid X receptor (FXR). FXR is a nuclear receptor which acts as a key regulator of cholesterol homeostasis, triglyceride synthesis and lipogenesis (Crawley, Expert Opinion Ther. Patents 2010, 20, 1047-1057). This receptor is expressed in various organs and shown to be involved in many diseases and conditions, including liver diseases, lung diseases, renal diseases, intestinal diseases, and heart diseases, and biological processes, such as glucose metabolism, insulin metabolism, and lipid metabolism.

Definitions

As used herein, "Compound 1" or "a compound of the invention" refers to 7α,11β-dihydroxy-6α-ethyl-5β-cholan-24-oic acid which has the following chemical structure:

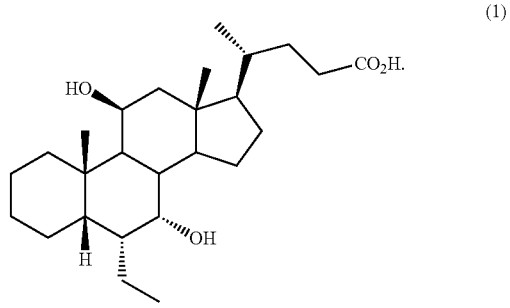 [SMILES: CC[C@H]1[C@@H](O)C2C3CC[C@H]([C@H](C)CCC(=O)O)[C@@]3(C)C[C@H](O)C2[C@@]2(C)CCCC[C@@H]12]

(1)

The invention also comprehends isotopically-labeled Compound 1, or pharmaceutically acceptable salts or amino acid conjugates thereof, which are identical to those recited in structure above but for the fact that one or more atoms are replaced by an atom having an atomic mass or mass number different from the atomic mass or mass number most commonly found in nature. Examples of isotopes that can be incorporated into the compound of the invention or pharmaceutically acceptable salts or amino acid conjugates thereof include isotopes of hydrogen, carbon, nitrogen, fluorine, such as $^3$H, $^{11}$C, $^{14}$C, and $^{18}$F.

Tritiated, i.e., $^3$H, and carbon-14, i.e., $^{14}$C, isotopes may be used for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be used in some circumstances. Isotopically labeled compounds or pharmaceutically acceptable salts or amino acid conjugates thereof can generally be prepared by carrying out the procedures disclosed in the Scheme and/or in the Examples, by substituting a readily available isotopically labeled reagent for a non-isotopically labeled reagent. However, one skilled in the art will recognize that not all isotopes can be included by substitution of the non-isotopically labeled reagent. In one embodiment, Compound 1 or pharmaceutically acceptable salts or amino acid conjugates thereof are not isotopically labeled. In one embodiment, deuterated Compound 1 or pharmaceutically acceptable salts or amino acid conjugates thereof are useful for bioanalytical assays. In another embodiment, Compound 1 or pharmaceutically acceptable salts or amino acid conjugates thereof are radiolabeled.

As used herein, "pharmaceutically acceptable salts" refer to derivatives of Compound 1 wherein the parent compound is modified by forming a salt of the carboxylic acid moiety. Examples of pharmaceutically acceptable salts include, but are not limited to, cations such as $Na^+$, $K^+$, $Ca^{2+}$, $Mg^{2+}$, and $NH_4^+$ are examples of cations present in pharmaceutically acceptable salts. Suitable inorganic bases include calcium hydroxide, potassium hydroxide, sodium carbonate and sodium hydroxide. Salts may also be prepared using organic bases, such as salts of primary, secondary and tertiary amines, substituted amines including naturally-occurring substituted amines, and cyclic amines including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier is "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, sunflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

A "composition" or "pharmaceutical composition" is a formulation containing a compound of the invention or a salt or amino acid conjugate thereof. In one embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or salts thereof) in a unit dose of composition is an effective amount and is varied according to the particular treatment involved. One skilled in the art will appreciate that it may be necessary to make routine variations to the dosage depending on the age and condition of the patient. The dosage will also depend on the route of administration. A variety of routes are contemplated, including oral, ocular, ophthalmic, pulmonary, rectal, parenteral, transdermal, subcutaneous, intravenous, intramuscular, intraperitoneal, intranasal, and the like. Dosage forms for the topical or transdermal administration of a compound of the invention include powders, sprays, ointments, pastes, creams, lotions, gels, solutions, patches and inhalants. In another embodiment, Compound 1 is mixed under sterile conditions with a pharmaceutically acceptable carrier, and with any preservatives, buffers, or propellants that are required.

The term "treating", as used herein, refers to relieving, lessening, reducing, eliminating, modulating, or ameliorating, i.e., causing regression of the disease state or condition.

The term "preventing", as used herein, refers to completely or almost completely stop a disease state or condition, from occurring in a patient or subject, especially when the patient or subject is predisposed to such or at risk of contracting a disease state or condition. Preventing can also include inhibiting, i.e., arresting the development, of a disease state or condition, and relieving or ameliorating, i.e., causing regression of the disease state or condition, for example when the disease state or condition may already be present.

The phrase "reducing the risk of", as used herein, refers to lowering the likelihood or probability of a central nervous system disease, inflammatory disease and/or metabolic disease from occurring in a patient, especially when the subject is predisposed to such occurrence.

"Combination therapy" (or "co-therapy") refers to the administration of a compound of the invention and at least a second agent as part of a specific treatment regimen intended to provide the beneficial effect from the co-action of these therapeutic agents (i.e., the compound of the invention and at least a second agent). The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected). "Combination therapy" may, but generally is not, intended to encompass the administration of two or more of these therapeutic agents as part of separate monotherapy regimens that incidentally and arbitrarily result in the combinations of the present application. "Combination therapy" is intended to embrace administration of this therapeutic agent in a sequential manner, that is, wherein the therapeutic agent is administered at a different time, as well as administration of this therapeutic agent, or at least two therapeutic agents, in a substantially simultaneous manner. Substantially simultaneous administration can be accomplished, for example, by administering to the subject a single capsule having a fixed ratio of a therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agent can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical.

"Combination therapy" also embraces the administration of the therapeutic agent as described above in further combination with other biologically active ingredients and non-drug therapies (e.g., surgery or mechanical treatments). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

An "effective amount" of a compound of the invention is an amount (quantity or concentration) of the compound to produce the desired pharmacological effect. In one embodiment, when an effective amount of a compound is administered to a subject in need of treatment symptoms arising from the disease are ameliorated immediately or after administration of the compound one or more times. The amount of the compound to be administered to a subject will depend on the particular disorder, the mode of administration, co-administered compounds, if any, and the characteristics of the subject, such as general health, other diseases, age, sex, genotype, body weight, and tolerance to drugs. The skilled artisan will be able to determine appropriate dosages depending on these and other factors.

The term "prophylactically effective amount" means an amount (quantity or concentration) of a compound of the present invention, or a combination of compounds, that is administered to prevent or reduce the risk of a disease—in other words, an amount needed to provide a preventative or prophylactic effect. The amount of the present compound to be administered to a subject will depend on the particular disorder, the mode of administration, co-administered compounds, if any, and the characteristics of the subject, such as general health, other diseases, age, sex, genotype, body weight, and tolerance to drugs. The skilled artisan will be able to determine appropriate dosages depending on these and other factors. A "subject" includes mammals, e.g., humans, companion animals (e.g., dogs, cats, birds, and the like), farm animals (e.g., cows, sheep, pigs, horses, and the like), and laboratory animals (e.g., rats, mice, guinea pigs, and the like). Typically, the subject is human.

Pharmaceutical Compositions

A "pharmaceutical composition" is a formulation containing a compound of the invention in a form suitable for administration to a subject. In one embodiment, the pharmaceutical composition is in bulk or in unit dosage form. It can be advantageous to formulate compositions in dosage unit form for ease of administration and uniformity of dosage. Dosage unit form as used herein refers to physically discrete units suited as unitary dosages for the subject to be treated; each unit containing a predetermined quantity of active reagent calculated to produce the desired therapeutic effect in association with the required pharmaceutical carrier. The specification for the dosage unit forms are dictated by and directly dependent on the unique characteristics of the active reagent and the particular therapeutic effect to be achieved, and the limitations inherent in the art of compounding such an active agent for the treatment of individuals.

Possible formulations include those suitable for oral, sublingual, buccal, parenteral (e.g., subcutaneous, intramuscular, or intravenous), rectal, topical including transdermal, intranasal and inhalation administration. Most suitable means of administration for a particular patient will depend on the nature and severity of the disease being treated or the nature of the therapy being used and on the nature of the active compound, but where possible, oral administration may be used for the prevention and treatment of FXR activated diseases and conditions. Formulations suitable for oral administration may be provided as discrete units, such as tablets, capsules, cachets, lozenges, each containing a predetermined amount of the active compound; as powders or granules; as solutions or suspensions in aqueous or non-aqueous liquids; or as oil-in-water or water-in-oil emulsions. Formulations suitable for sublingual or buccal administration include lozenges comprising the active compound and, typically a flavored base, such as sugar and acacia or tragacanth and pastilles comprising the active compound in an inert base, such as gelatin and glycerin or sucrose acacia.

Formulations suitable for parenteral administration typically comprise sterile aqueous solutions containing a predetermined concentration of the active compound; the solution may be isotonic with the blood of the intended recipient. Additional formulations suitable for parenteral administration include formulations containing physiologically suitable co-solvents and/or complexing agents such as surfactants and cyclodextrins. Oil-in-water emulsions are also suitable formulations for parenteral formulations. Although such solutions may be administered intravenously, they may also be administered by subcutaneous or intramuscular injection.

Formulations suitable for rectal administration may be provided as unit-dose suppositories comprising the active ingredient in one or more solid carriers forming the suppository base, for example, cocoa butter.

Formulations suitable for topical or intranasal application include ointments, creams, lotions, pastes, gels, sprays, aerosols, and oils. Suitable carriers for such formulations include petroleum jelly, lanolin, polyethyleneglycols, alcohols, and combinations thereof.

Formulations of the invention may be prepared by any suitable method, typically by uniformly and intimately admixing the active compound with liquids or finely divided solid carriers or both, in the required proportions and then, if necessary, shaping the resulting mixture into the desired shape.

For example, a tablet may be prepared by compressing an intimate mixture comprising a powder or granules of the active ingredient and one or more optional ingredients, such as a binder, lubricant, inert diluent, or surface active dispersing agent, or by molding an intimate mixture of powdered active ingredient and inert liquid diluent. Suitable formulations for administration by inhalation include fine particle dusts or mists which may be generated by means of various types of metered dose pressurized aerosols, nebulizers, or insufflators.

For pulmonary administration via the mouth, the particle size of the powder or droplets is typically in the range of 0.5-10 µm, or may be about 1-5 µm, to ensure delivery into the bronchial tree. For nasal administration, a particle size in the range of 10-500 µm may be used to ensure retention in the nasal cavity.

Metered dose inhalers are pressurized aerosol dispensers, typically containing a suspension or solution formulation of the active ingredient in a liquefied propellant. During use, these devices discharge the formulation through a valve adapted to deliver a metered volume, typically from 10 to 150 µm, to produce a fine particle spray containing the active ingredient. Suitable propellants include certain chlorofluorocarbon compounds, for example, dichlorodifluoromethane, trichlorofluoromethane, dichlorotetrafluoroethane, and mixtures thereof. The formulation may additionally contain one or more co-solvents, for example, ethanol surfactants, such as oleic acid or sorbitan trioleate, anti-oxidants and suitable flavoring agents.

Nebulizers are commercially available devices that transform solutions or suspensions of the active ingredient into a therapeutic aerosol mist either by means of acceleration of a compressed gas typically air or oxygen, through a narrow venturi orifice, or by means of ultrasonic agitation. Suitable formulations for use in nebulizers consist of the active ingredient in a liquid carrier and comprise up to 40% w/w of the formulation, preferably less than 20% w/w. The carrier is typically water or a dilute aqueous alcoholic solution, preferably made isotonic with body fluids by the addition of, for example, sodium chloride. Optional additives include preservatives if the formulation is not prepared sterile, for example, methyl hydroxy-benzoate, anti-oxidants, flavoring agents, volatile oils, buffering agents, and surfactants.

Suitable formulations for administration by insufflation include finely comminuted powders which may be delivered by means of an insufflator or taken into the nasal cavity in the manner of a snuff. In the insufflator, the powder is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the active ingredient or of a powder blend comprising the active ingredient, a suitable powder diluent, such as lactose, and an optional surfactant. The active ingredient typically comprises from 0.1 to 100% w/w of the formulation.

In a further embodiment, the present invention provides a pharmaceutical composition comprising, as active ingredient, a compound of the invention together, and/or in admixture, with at least one pharmaceutical carrier or diluent. These pharmaceutical compositions may be used in the prevention or treatment of the foregoing diseases or conditions.

The carrier is pharmaceutically acceptable and must be compatible with, i.e. not have a deleterious effect upon, the other ingredients in the composition. The carrier may be a solid or liquid and is preferably formulated as a unit dose formulation, for example, a tablet which may contain from 0.05 to 95% by weight of the active ingredient. If desired, other physiologically active ingredients may also be incorporated in the pharmaceutical compositions of the invention.

In addition to the ingredients specifically mentioned above, the formulations of the present invention may include other agents known to those skilled in the art of pharmacy, having regard for the type of formulation in issue. For example, formulations suitable for oral administration may include flavoring agents and formulations suitable for intranasal administration may include perfumes.

Methods of Treatment

The compound of the invention is useful for therapy in subjects such as mammals, including humans. In particular, the compound of the invention is useful in a method of treating or preventing a disease or condition in a subject comprising administering to the subject in need thereof an effective amount of a compound of the invention or a pharmaceutically acceptable salt or amino acid conjugate thereof. In one embodiment, the disease or condition is activated by FXR-activation (e.g., FXR plays a role in the initiation or progress of the disease or condition). In one embodiment, the disease or condition is selected from cardiovascular disease, chronic liver disease, lipid disorder, gastrointestinal disease, renal disease, metabolic disease, cancer, and neurological disease.

In one embodiment, the invention relates to a method of treating or preventing cardiovascular disease in a subject, comprising administering to the subject in need thereof an effective amount of a compound of the invention or a pharmaceutically acceptable salt or amino acid conjugate thereof. In one embodiment, the invention relates to a method of treating cardiovascular disease. In one embodiment, cardiovascular disease selected from atherosclerosis, arteriosclerosis, dyslipidemia, hypercholesteremia, hyperlipidemia, hyperlipoproteinemia, and hypertriglyceridemia.

The term "hyperlipidemia" refers to the presence of an abnormally elevated level of lipids in the blood. Hyperlipidemia can appear in at least three forms: hypercholesterolemia, i.e., an elevated cholesterol level; hypertriglyceridemia, i.e., an elevated triglyceride level; and combined hyperlipidemia, i.e., a combination of hypercholesterolemia and hypertriglyceridemia.

The term "dyslipidemia" refers to abnormal levels of lipoproteins in blood plasma including both depressed and/or elevated levels of lipoproteins (e.g., elevated levels of LDL, VLDL and depressed levels of HDL).

In one embodiment, the invention relates to a method selected from reducing cholesterol levels or modulating cholesterol metabolism, catabolism, absorption of dietary cholesterol, and reverse cholesterol transport in a subject, comprising administering to the subject in need thereof an effective amount of a compound of the invention or a pharmaceutically acceptable salt or amino acid conjugate thereof.

In another embodiment, the invention relates to a method of treating or preventing a disease affecting cholesterol, triglyceride, or bile acid levels in a subject, comprising administering to the subject in need thereof an effective amount of a compound of the invention or a pharmaceutically acceptable salt or amino acid conjugate thereof.

In one embodiment, the invention relates to a method of lowering triglycerides in a subject, comprising administering to the subject in need thereof an effective amount of a compound of the invention or a pharmaceutically acceptable salt or amino acid conjugate thereof.

In one embodiment, the invention relates to a method of treating or preventing a disease state associated with an elevated cholesterol level in a subject, comprising administering to the subject in need thereof an effective amount of Compound 1 or a pharmaceutically acceptable salt or amino acid conjugate thereof. In one embodiment, the invention relates to a method of treating a disease state associated with an elevated cholesterol level in a subject. In one embodiment, the invention relates to a method of preventing a disease state associated with an elevated cholesterol level in a subject. In one embodiment, the disease state is selected from coronary artery disease, angina pectoris, carotid artery disease, strokes, cerebral arteriosclerosis, and xanthoma.

In one embodiment, the invention relates to a method of treating or preventing a lipid disorder in a subject, comprising administering to the subject in need thereof an effective amount of Compound 1 or a pharmaceutically acceptable salt or amino acid conjugate thereof. In one embodiment, the invention relates to a method of treating a lipid disorder. In one embodiment, the invention relates to a method of preventing a lipid disorder.

Lipid disorders are the term for abnormalities of cholesterol and triglycerides. Lipid abnormalities are associated with an increased risk for vascular disease, and especially heart attacks and strokes. Abnormalities in lipid disorders are a combination of genetic predisposition as well as the nature of dietary intake. Many lipid disorders are associated with being overweight. Lipid disorders may also be associated with other diseases including diabetes, the metabolic syndrome (sometimes called the insulin resistance syndrome), underactive thyroid or the result of certain medications (such as those used for anti-rejection regimens in people who have had transplants).

In one embodiment, the invention relates to a method of treating or preventing one or more symptoms of disease affecting lipid metabolism (i.e., lipodystrophy) in a subject, comprising administering to the subject in need thereof an effective amount of a compound of the invention or a pharmaceutically acceptable salt or amino acid conjugate thereof. In one embodiment, the invention relates to a method of treating one or more symptoms of a disease affecting lipid metabolism. In one embodiment, the invention relates to a method of preventing one or more symptoms of a disease affecting lipid metabolism.

In one embodiment, the invention relates to a method of decreasing lipid accumulation in a subject, comprising administering to the subject in need thereof an effective amount of a compound of the invention or a pharmaceutically acceptable salt or amino acid conjugate thereof.

In one embodiment, the invention relates to a method of treating or preventing chronic liver disease in a subject, comprising administering to the subject in need thereof an effective amount of a compound of the invention or a pharmaceutically acceptable salt or amino acid conjugate thereof. In one embodiment, the invention relates to a method of treating chronic liver disease. In one embodiment, the invention relates to a method of preventing chronic liver disease. In one embodiment, the chronic liver disease is selected from primary biliary cirrhosis (PBC) (also known as primary biliary cholangitis (PBC)), cerebrotendinous xanthomatosis (CTX), primary sclerosing cholangitis (PSC), drug induced cholestasis, intrahepatic cholestasis of pregnancy, parenteral nutrition associated cholestasis (PNAC), bacterial overgrowth or sepsis associated cholestasis, autoimmune hepatitis, chronic viral hepatitis, alcoholic liver disease, nonalcoholic fatty liver disease (NAFLD), nonalcoholic steatohepatitis (NASH), liver transplant associated graft versus host disease, living donor transplant liver regeneration, congenital hepatic fibrosis, choledocholithiasis, granulomatous liver disease, intra- or extrahepatic malignancy, Sjogren's syndrome, Sarcoidosis, Wilson's disease, Gaucher's disease, hemochromatosis, and alpha1-antitrypsin deficiency.

In one embodiment, the invention relates to a method of treating or preventing one or more symptoms of cholestasis, including complications of cholestasis in a subject, comprising administering to the subject in need thereof an effective amount of a compound of the invention or a pharmaceutically acceptable salt or amino acid conjugate thereof. In one embodiment, the invention relates to a method of treating one or more symptoms of cholestasis. In one embodiment, the invention relates to preventing one or more symptoms of cholestasis.

Cholestasis is typically caused by factors within the liver (intrahepatic) or outside the liver (extrahepatic) and leads to the accumulation of bile salts, bile pigment bilirubin, and lipids in the blood stream instead of being eliminated normally. Intrahepatic cholestasis is characterized by widespread blockage of small ducts or by disorders, such as hepatitis, that impair the body's ability to eliminate bile. Intrahepatic cholestasis may also be caused by alcoholic liver disease, primary biliary cirrhosis, cancer that has spread (metastasized) from another part of the body, primary sclerosing cholangitis, gallstones, biliary colic, and acute cholecystitis. It can also occur as a complication of surgery, serious injury, cystic fibrosis, infection, or intravenous feeding or be drug induced. Cholestasis may also occur as a complication of pregnancy and often develops during the second and third trimesters. Extrahepatic cholestasis is most often caused by choledocholithiasis (Bile Duct Stones), benign biliary strictures (non-cancerous narrowing of the common duct), cholangiocarcinoma (ductal carcinoma), and pancreatic carcinoma. Extrahepatic cholestasis can occur as a side effect of many medications.

A compound of the invention may be used for treating or preventing one or more symptoms of intrahepatic or extrahepatic cholestasis, including without limitation, biliary atresia, obstetric cholestasis, neonatal cholestasis, drug induced cholestasis, cholestasis arising from Hepatitis C infection, chronic cholestatic liver disease such as primary biliary cirrhosis (PBC), and primary sclerosing cholangitis (PSC).

In one embodiment, the invention relates to a method of enhancing liver regeneration in a subject, comprising administering to the subject in need thereof an effective amount of a compound of the invention or a pharmaceutically acceptable salt or amino acid conjugate thereof. In one embodiment, the method is enhancing liver regeneration for liver transplantation.

In one embodiment, the invention relates to a method of treating or preventing fibrosis in a subject, comprising administering to the subject in need thereof an effective amount of a compound of the invention or a pharmaceutically acceptable salt or amino acid conjugate thereof. In one embodiment, the invention relates to a method of treating fibrosis. In one embodiment, the invention relates to a method of preventing fibrosis.

Accordingly, as used herein, the term fibrosis refers to all recognized fibrotic disorders, including fibrosis due to pathological conditions or diseases, fibrosis due to physical trauma ("traumatic fibrosis"), fibrosis due to radiation damage, and fibrosis due to exposure to chemotherapeutics. As used herein, the term "organ fibrosis" includes but is not limited to liver fibrosis, fibrosis of the kidneys, fibrosis of lung, and fibrosis of the intestine. "Traumatic fibrosis" includes but is not limited to fibrosis secondary to surgery (surgical scarring), accidental physical trauma, burns, and hypertrophic scarring.

As used herein, "liver fibrosis" includes liver fibrosis due to any cause, including but not limited to virally-induced liver fibrosis such as that due to hepatitis B or C virus; exposure to alcohol (alcoholic liver disease), certain pharmaceutical compounds including but not limited to methotrexate, some chemotherapeutic agents, and chronic ingestion of arsenicals or vitamin A in megadoses, oxidative stress, cancer radiation therapy or certain industrial chemicals including but not limited to carbon tetrachloride and dimethylnitrosamine; and diseases such as primary biliary cirrhosis, primary sclerosing cholangitis, fatty liver, obesity, non-alcoholic steatohepatitis, cystic fibrosis, hemochromatosis, auto-immune hepatitis, and steatohepatitis. Current therapy in liver fibrosis is primarily directed at removing the causal agent, e.g., removing excess iron (e.g., in the case of hemochromatosis), decreasing viral load (e.g., in the case of chronic viral hepatitis), or eliminating or decreasing exposure to toxins (e.g., in the case of alcoholic liver disease). Anti-inflammatory drugs such as corticosteroids and colchicine are also known for use in treating inflammation that can lead to liver fibrosis. As is known in the art, liver fibrosis may be clinically classified into five stages of severity (S0, S1, S2, S3, and S4), usually based on histological examination of a biopsy specimen. S0 indicates no fibrosis, whereas S4 indicates cirrhosis. While various criteria for staging the severity of liver fibrosis exist, in general early stages of fibrosis are identified by discrete, localized areas of scarring in one portal (zone) of the liver, whereas later stages of fibrosis are identified by bridging fibrosis (scarring that crosses zones of the liver).

In one embodiment, the invention relates to a method of treating or preventing organ fibrosis in a subject, comprising administering to the subject in need thereof an effective amount of a compound of the invention or a pharmaceutically acceptable salt or amino acid conjugate thereof. In one embodiment, the fibrosis is liver fibrosis.

In one embodiment, the invention relates to a method of treating or preventing gastrointestinal disease in a subject, comprising administering to the subject in need thereof an effective amount of a compound of the invention or a pharmaceutically acceptable salt or amino acid conjugate thereof. In one embodiment, the invention relates to a method of treating gastrointestinal disease. In one embodiment, the invention relates to a method of preventing gastrointestinal disease. In one embodiment, the gastrointestinal disease is selected from inflammatory bowel disease (IBD), irritable bowel syndrome (IBS), bacterial overgrowth, malabsorption, post-radiation colitis, and microscopic colitis. In one embodiment, the inflammatory bowel disease is selected from Crohn's disease and ulcerative colitis.

In one embodiment, the invention relates to a method of treating or preventing renal disease in a subject, comprising administering to the subject in need thereof an effective amount of a compound of the invention or a pharmaceutically acceptable salt or amino acid conjugate thereof. In one embodiment, the invention relates to a method of treating renal disease. In one embodiment, the invention relates to a method of preventing renal disease. In one embodiment, the renal disease is selected from diabetic nephropathy, focal segmental glomerulosclerosis (FSGS), hypertensive nephrosclerosis, chronic glomerulonephritis, chronic transplant glomerulopathy, chronic interstitial nephritis, and polycystic kidney disease.

In one embodiment, the invention relates to a method of treating or preventing metabolic disease in a subject, comprising administering to the subject in need thereof an effective amount of a compound of the invention or a pharmaceutically acceptable salt or amino acid conjugate thereof. In one embodiment, the invention relates to a method of treating renal disease. In one embodiment, the invention relates to a method of preventing renal disease. In one embodiment, the metabolic disease is selected from insulin resistance, hyperglycemia, diabetes mellitus, diabesity, and obesity. In one embodiment, the diabetes mellitus is type I diabetes. In one embodiment, the diabetes mellitus is type II diabetes.

Diabetes mellitus, commonly called diabetes, refers to a disease or condition that is generally characterized by metabolic defects in production and utilization of glucose which result in the failure to maintain appropriate blood sugar levels in the body.

In the case of type II diabetes, the disease is characterized by insulin resistance, in which insulin loses its ability to exert its biological effects across a broad range of concentrations. This resistance to insulin responsiveness results in insufficient insulin activation of glucose uptake, oxidation and storage in muscle and inadequate insulin repression of lipolysis in adipose tissue and of glucose production and secretion in liver. The resulting condition is elevated blood glucose, which is called "hyperglycemia". Uncontrolled hyperglycemia is associated with increased and premature mortality due to an increased risk for microvascular and macrovascular diseases, including retinopathy (the impairment or loss of vision due to blood vessel damage in the eyes); neuropathy (nerve damage and foot problems due to blood vessel damage to the nervous system); and nephropathy (kidney disease due to blood vessel damage in the kidneys), hypertension, cerebrovascular disease, and coronary heart disease. Therefore, control of glucose homeostasis is a critically important approach for the treatment of diabetes.

Insulin resistance has been hypothesized to unify the clustering of hypertension, glucose intolerance, hyperinsulinemia, increased levels of triglyceride and decreased HDL cholesterol, and central and overall obesity. The association of insulin resistance with glucose intolerance, an increase in plasma triglyceride and a decrease in high-density lipoprotein cholesterol concentrations, hypertension, hyperuricemia, smaller denser low-density lipoprotein particles, and higher circulating levels of plasminogen activator inhibitor-1, has been referred to as "Syndrome X". Accordingly, methods of treating or preventing any disorders related to insulin resistance including the cluster of disease states, conditions or disorders that make up "Syndrome X" are provided. In one embodiment, the invention relates to a method of treating or preventing metabolic syndrome in a subject, comprising administering to the subject in need thereof an effective amount of a compound of the invention or a pharmaceutically acceptable salt or amino acid conjugate thereof. In one embodiment, the invention relates to a method of treating metabolic syndrome. In another embodiment, the invention relates to a method of preventing metabolic syndrome.

In one embodiment, the invention relates to a method of treating or preventing cancer in a subject, comprising administering to the subject in need thereof an effective amount of a compound of the invention or a pharmaceutically acceptable salt or amino acid conjugate thereof. In one embodiment, the invention relates to a method of treating cancer. In one embodiment, the invention relates to a method of preventing cancer. In one embodiment, the cancer is selected from hepatocellular carcinoma, colorectal cancer, gastric cancer, renal cancer, prostate cancer, adrenal cancer, pancreatic cancer, breast cancer, bladder cancer, salivary gland cancer, ovarian cancer, uterine body cancer, and lung cancer. In one embodiment, the cancer is hepatocellular carcinoma. In one embodiment, the cancer is colorectal cancer. In one embodiment, the cancer is gastric cancer. In one embodiment, the cancer is renal cancer. In one embodiment, the cancer is prostate cancer. In one embodiment, the cancer is adrenal cancer. In one embodiment, the cancer is pancreatic cancer. In one embodiment, the cancer is breast cancer. In one embodiment, the cancer is bladder cancer. In one embodiment, the cancer is salivary gland cancer. In one embodiment, the cancer is ovarian cancer. In one embodiment, the cancer is uterine body cancer. In one embodiment, the cancer is lung cancer.

In another embodiment, at least one of an agent selected from Sorafenib, Sunitinib, Erlotinib, or Imatinib is co-administered with the compound of the invention to treat cancer. In one embodiment, at least one of an agent selected from abarelix, aldeleukin, allopurinol, altretamine, amifostine, anastozole, bevacizumab, capecitabine, carboplatin, cisplatin, docetaxel, doxorubicin, erlotinib, exemestane, 5-fluorouracil, fulvestrant, gemcitabine, goserelin acetate, irinotecan, lapatinib ditosylate, letozole, leucovorin, levamisole, oxaliplatin, paclitaxel, panitumumab, pemetrexed disodium, profimer sodium, tamoxifen, topotecan, and trastuzumab is co-administered with the compound of the invention to treat cancer.

Appropriate treatment for cancers depends on the type of cell from which the tumor derived, the stage and severity of the malignancy, and the genetic abnormality that contributes to the tumor.

Cancer staging systems describe the extent of cancer progression. In general, the staging systems describe how far the tumor has spread and puts patients with similar prognosis and treatment in the same staging group. In general, there are poorer prognoses for tumors that have become invasive or metastasized.

In one type of staging system, cases are grouped into four stages, denoted by Roman numerals I to IV. In stage I, cancers are often localized and are usually curable. Stage II and IIIA cancers are usually more advanced and may have invaded the surrounding tissues and spread to lymph nodes. Stage IV cancers include metastatic cancers that have spread to sites outside of lymph nodes.

Another staging system is TNM staging which stands for the categories: Tumor, Nodes, and Metastases. In this system, malignancies are described according to the severity of the individual categories. For example, T classifies the extent of a primary tumor from 0 to 4 with 0 representing a malignancy that does not have invasive activity and 4 representing a malignancy that has invaded other organs by extension from the original site. N classifies the extent of lymph node involvement with 0 representing a malignancy with no lymph node involvement and 4 representing a malignancy with extensive lymph node involvement. M classifies the extent of metastasis from 0 to 1 with 0 representing a malignancy with no metastases and 1 representing a malignancy with metastases.

These staging systems or variations of these staging systems or other suitable staging systems may be used to describe a tumor such as hepatocellular carcinoma. Few options only are available for the treatment of hepatocellular cancer depending on the stage and features of the cancer. Treatments include surgery, treatment with Sorafenib, and targeted therapies. In general, surgery is the first line of treatment for early stage localized hepatocellular cancer. Additional systemic treatments may be used to treat invasive and metastatic tumors.

In one embodiment, the invention relates to a method of treating or preventing gallstones in a subject, comprising administering to the subject in need thereof an effective amount of a compound of the invention or a pharmaceutically acceptable salt or amino acid conjugate thereof. In one embodiment, the invention relates to a method of treating gallstones. In one embodiment, the invention relates to a method of preventing gallstones.

A gallstone is a crystalline concretion formed within the gallbladder by accretion of bile components. These calculi are formed in the gallbladder but may distally pass into other parts of the biliary tract such as the cystic duct, common bile duct, pancreatic duct, or the ampulla of Vater. Rarely, in cases of severe inflammation, gallstones may erode through the gallbladder into adherent bowel potentially causing an obstruction termed gallstone ileus. Presence of gallstones in the gallbladder may lead to acute cholecystitis, an inflammatory condition characterized by retention of bile in the gallbladder and often secondary infection by intestinal microorganisms, predominantly *Escherichia coli*, and *Bacteroides* species.

Presence of gallstones in other parts of the biliary tract can cause obstruction of the bile ducts, which can lead to serious conditions such as ascending cholangitis or pancreatitis. In one embodiment, the invention relates to a method of treating or preventing cholesterol gallstone disease in a subject, comprising administering to the subject in need thereof an effective amount of a compound of the invention or a pharmaceutically acceptable salt or amino acid conjugate thereof. In one embodiment, the invention relates to a method of treating cholesterol gallstone disease. In one embodiment, the invention relates to a method of preventing cholesterol gallstone disease.

In one embodiment, the invention relates to a method of treating or preventing neurological disease in a subject, comprising administering to the subject in need thereof an effective amount of a compound of the invention or a pharmaceutically acceptable salt or amino acid conjugate thereof. In one embodiment, the invention relates to a method of treating neurological disease. In one embodiment, the invention relates to a method of preventing neurological disease. In one embodiment, the neurological disease is stroke.

In one embodiment, the invention relates to a method as described herein and further wherein, the compound is administered by a route selected from oral, parenteral, intramuscular, intranasal, sublingual, intratracheal, inhalation, ocular, vaginal, rectal, and intracerebroventricular. In one embodiment, the route is oral.

In one embodiment, the compound utilized in one or more of the methods described herein is an FXR agonist. In one embodiment, the compound is a selective FXR agonist. In another embodiment, the compound does not activate TGR5. In one embodiment, the compound does not activate other nuclear receptors involved in metabolic pathways (e.g., as measured by an AlphaScreen assay). In one embodiment, such other nuclear receptors involved in metabolic pathways are selected from LXRβ, PXR, CAR, PPARα, PPARδ, PPARγ, RAR, RARα, VDR, TR, PR, RXR, GR, and ER. In one embodiment, the compound induces apoptosis.

In one embodiment, the invention relates to a method of regulating the expression level of one or more genes involved in bile acid homeostasis.

In one embodiment, the invention relates to a method of down regulating the expression level of one or more genes selected from CYP7α1 and SREBP-IC in a cell by administering to the cell a compound of the invention. In one embodiment, the invention relates to a method of up regulating the expression level of one or more genes selected from OSTα, OSTβ, BSEP, SHP, UGT2B4, MRP2, FGF-19, PPARγ, PLTP, APOCII, and PEPCK in a cell by administering to the cell a compound of the invention.

The invention also relates to the manufacture of a medicament for treating or preventing a disease or condition (e.g., a disease or condition activated by FXR), wherein the medicament comprises a compound of the invention or a pharmaceutically acceptable salt or amino acid conjugate thereof. In one embodiment, the invention relates to the manufacture of a medicament for treating or preventing any one of the diseases or conditions described herein above, wherein the medicament comprises a compound of the invention or a pharmaceutically acceptable salt or amino acid conjugate thereof.

The invention also relates to a composition for use in a method for treating or preventing a disease or condition (e.g., a disease or condition activated by FXR), wherein the composition comprises a compound of the invention or a pharmaceutically acceptable salt or amino acid conjugate thereof. In one embodiment, the invention relates to a composition for use in a method for treating or preventing any one of the diseases or conditions described herein above, wherein the composition comprises a compound of the invention or a pharmaceutically acceptable salt or amino acid conjugate thereof.

The methods of the invention comprise the step of administering an effective amount of a compound of the invention. As used herein, the term an "effective amount" refers to an amount of a compound of the invention which is sufficient to achieve the stated effect. Accordingly, an effective amount of a compound of the invention used in a method for the prevention or treatment of FXR activated diseases or conditions will be an amount sufficient to prevent or treat the FXR activated disease or condition.

Similarly, an effective amount of a compound of the invention for use in a method for the prevention or treatment of a cholestatic liver disease or increasing bile flow will be an amount sufficient to increase bile flow to the intestine.

The amount of the compound of the invention which is required to achieve the desired biological effect will depend on a number of factors such as the use for which it is intended, the means of administration, and the recipient, and will be ultimately at the discretion of the attendant physician or veterinarian. In general, a typical daily dose for the treatment of a FXR activated disease and condition, for instance, may be expected to lie in the range of from about 0.01 mg/kg to about 100 mg/kg. This dose may be administered as a single unit dose or as several separate unit doses or as a continuous infusion. Similar dosages would be applicable for the treatment of other diseases, conditions and therapies including the prevention and treatment of cholestatic liver diseases.

EXPERIMENTAL SECTION

Example 1. Synthesis of Compound 1

Compound 1 was prepared according to the procedures described in Scheme 1 and from 7α,11β-dihydroxy-6α-ethyl-5β-cholan-24-oic acid (A1) as the starting material. A1 was prepared by methods known in the art. For example, A1 can be prepared by the procedures described in PCT Publication No. WO 2014/184271.

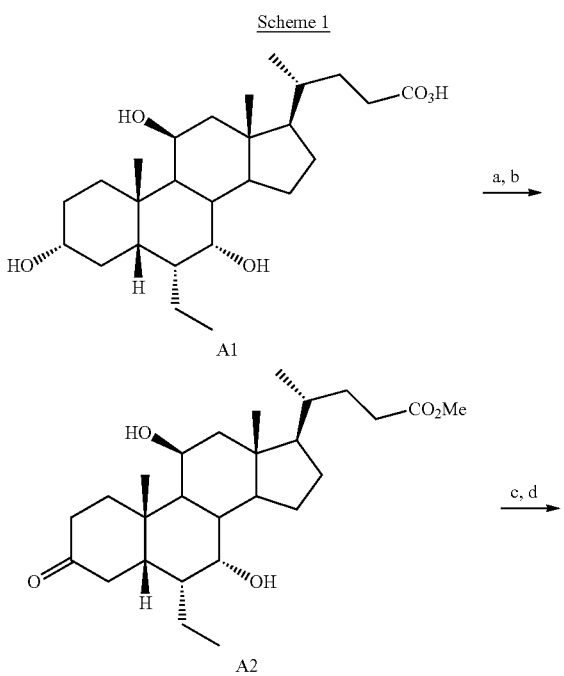

Scheme 1

-continued

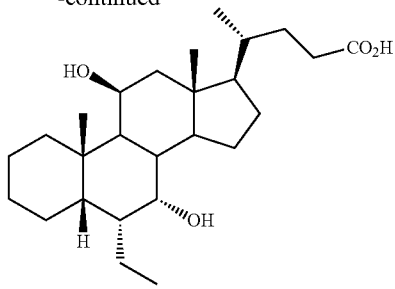
1

Reagents and conditions: A) MeOH, p-TSA; b) Fetizon's Reagent, dry toluene, reflux; c) NaOH, MeOH; d) KOH, NH₂NH₂·H₂O, ethylene glycol, reflux.

Methyl 7α,11β-dihydroxy-6α-ethyl-3-oxo-5β-cholan-24-oate (A2)

A solution of A1 (0.46 mmol) and p-TSA (0.046 mmol) in MeOH (5 mL) was reacted overnight. The solvent was removed under reduced pressure, the residue was dissolved in ethyl acetate (10 mL) and washed with a saturated solution of NaHCO₃ up to neutral pH. The aqueous phase was extracted with EtOAc and the combined organic layers washed with brine, dried over anhydrous Na₂SO₄ and concentrated under vacuum. The crude was dissolved in toluene (6.5 mL) and refluxed with Fetizon's reagent for 18 h. The mixture was filtered on a Celite pad, the filtrate concentrated under vacuum and used for the next step without further purifications.

$^1$H-NMR (400 MHz, CDCl₃): δ 0.87-0.95 (9H, m, CH₃-18, CH₃-21, CH₃-26), 1.23 (3H, s, CH₃-19), 3.0 (1H, t, J=14.2 Hz, CH-4), 3.65 (3H, s, COOCH₃), 3.87 (1H, s, CH-7), 4.32 (1H, s, CH-11).

7α,11β-Dihydroxy-6α-ethyl-5β-cholan-24-oic acid (1)

Methyl 7α,11β-dihydroxy-6α-ethyl-3-oxo-5β-cholan-24-oate (A2) (150 mg) was stirred with a methanolic solution of NaOH overnight. The solvent was evaporated under reduced pressure and the residual dissolved in water and washed with Et₂O. The aqueous phase was acidified with HCl 3 N up to pH 1, extracted with CHCl₃ and the collected organic layers washed with H₂O, brine, dried over anhydrous Na₂SO₄ and concentrated under vacuum. The crude was purified by flash chromatography on silica gel using a mixture of petroleum ether and ethyl acetate as eluting solvent system. A suspension of 7α,11β-dihydroxy-6α-ethyl-3-oxo-5β-cholan-24-oic acid (0.21 mmol) in ethylene glycol (2 mL) was refluxed for 30 h with KOH (0.518 mmol) and NH₂NH₂.H₂O (2.07 mmol). The mixture was cooled to room temperature, diluted with H₂O and washed with Et₂O (3×5 mL). After acidification with HCl 3 N up to pH 1, the aqueous phase was extracted with EtOAc and the collected organic layers washed with H₂O, brine, dried over anhydrous Na₂SO₄ and concentrated under reduced pressure. The crude was purified by reverse phase C18 flash chromatography using H₂O-MeOH as eluting solvent system thus obtaining 7α,11β-dihydroxy-6α-ethyl-5β-cholan-24-oic acid (1) as a white solid.

$^1$H-NMR (400 MHz, CD₃OD): δ 0.87-0.92 (6H, m, CH₃-18, CH₃-25), 1.00 (3H, d, J=6.4 Hz, CH₃-21), 1.14 (3H, s, CH₃-19), 3.73 (1H, s, CH-7), 4.19 (1H, s, CH-11).
$^{13}$C-NMR (100.6 MHz, CD₃OD): 12.1, 14.7, 19.0, 23.2, 23.5, 24.7, 25.5, 28.6, 29.0, 29.1, 34.1, 36.3, 37.5, 37.8, 38.3, 38.5, 38.8, 42.8 (×2), 50.1, 51.5, 52.3, 58.1, 69.3, 71.8, 183.6.

Pharmacology and Biological Data

In general, the prospect of a compound as a drug candidate may be evaluated using various assays known in the art. For example, for the in vitro validation of FXR, its activity and selectivity can be evaluated using AlphaScreen (biochemical assay); gene expression can be evaluated using RT-PCR (FXR target gene); and cytotoxicity (e.g., HepG2) can be evaluated using ATP content, LDH release, and Caspase-3 activation. For the in vitro validation for TGR5, its activity and selectivity can be evaluated using HTR-FRET (cell-based assay); gene expression can be evaluated using RT-PCR (TGR5 target gene (i.e., cFOS)); and cytotoxicity (e.g., HepG2) can be evaluated using ATP content, LDH release, and Caspase-3 activation. The following compounds were used as controls in the examples below.

As used herein Compound A is

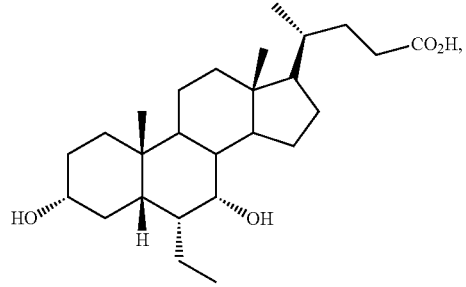

which is also known as obeticholic acid, INT-747, 6-ECDCA, 6-alpha-ethyl chenodeoxycholic acid, or 6α-ethyl-3α,7α-dihydroxy-5β-cholan-24-oic acid.

As used herein Compound B is

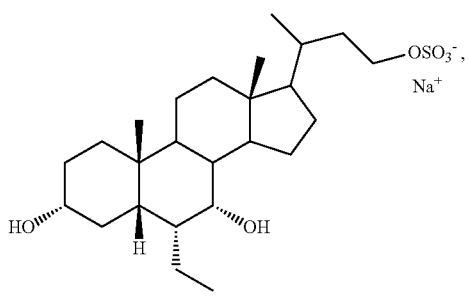

which is also known as INT-767 or 6α-ethyl-3α,7α,23-trihydroxy-24-nor-5β-cholan-23-sulfate sodium salt.

As used herein, Compound C is

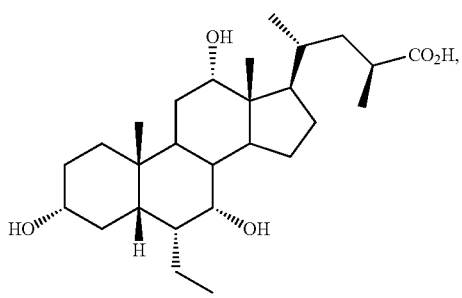 [SMILES: CC[C@H]1[C@@H](O)C2C3CC[C@H]([C@H](C)C[C@H](C)C(=O)O)[C@@]3(C)[C@@H](O)CC2[C@@]2(C)CC[C@@H](O)C[C@@H]12]

which is also known as INT-777 or 6α-ethyl-23(S)-methyl-3α,7α,12α trihydroxy-5β-cholan-24-oic acid.

As used herein, Compound D is

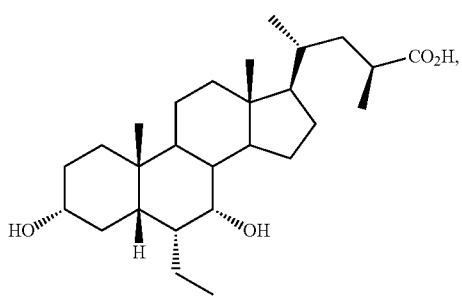 [SMILES: CC[C@H]1[C@@H](O)C2C3CC[C@H]([C@H](C)C[C@H](C)C(=O)O)[C@@]3(C)CCC2[C@@]2(C)CC[C@@H](O)C[C@@H]12]

which is also known as 6c-ethyl-23(R)-methyl chenodeoxycholic acid, and S-EMCDCA.

As used herein, Compound E is

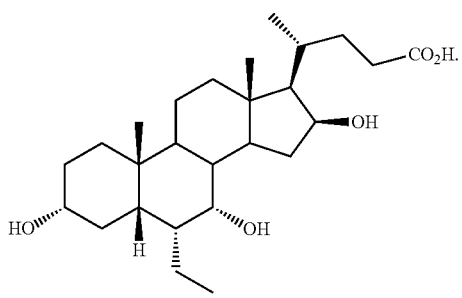 [SMILES: CC[C@H]1[C@@H](O)C2C3C[C@H](O)[C@H]([C@H](C)CCC(=O)O)[C@@]3(C)CCC2[C@@]2(C)CC[C@@H](O)C[C@@H]12]

As used herein, Compound F is

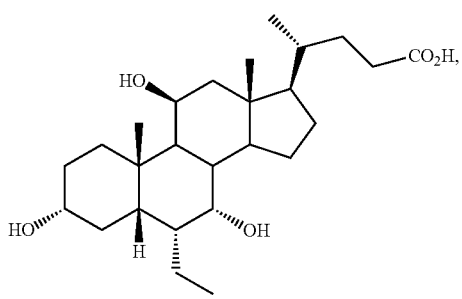 [SMILES: CC[C@H]1[C@@H](O)C2C3CC[C@H]([C@H](C)CCC(=O)O)[C@@]3(C)C[C@H](O)C2[C@@]2(C)CC[C@@H](O)C[C@@H]12]

which is also known as 3α,7α,11β-dihydroxy-6α-ethyl-5β-cholan-24-oic acid.

Example 2. FXR/TGR5 Activity

In the nucleus, ligand-bound nuclear receptors (NRs) modulate initiation of transcription by directly interacting with the basal transcriptional machinery or by contacting bridging factors called coactivators (Onate, et al., Science, 1995, 270, 1354-1357; Wang, et al., J Biol Chem, 1998, 273, 30847-30850; and Zhu, et al., Gene Expr, 1996, 6, 185-195). The ligand-dependent interaction of NRs with their coactivators occurs between activation function 2 (AF-2), located in the receptor ligand-binding domain (LBD) and the nuclear receptor boxes (NR box), located on the coactivators (Nolte, et al., Nature, 1998, 395, 137-143). Several lines of evidence have demonstrated that the LXXLL peptide sequence present in the NR box represents a signature motif that facilitates the interaction of different proteins with the AF-2 region (Heery, et al., Nature, 1997, 387, 733-736; and Torchia, et al., Nature, 1997, 387, 677-684).

AlphaScreen was used with the aim of identifying novel modulators by taking advantage of the bimolecular interaction prevailing between FXR and the LXXLL motif present in the NR box of the steroid receptor coactivator 1 (SRC-1).

Human FXR-LBD-GST was incubated with increasing concentrations of the indicated ligands in the presence of biotinylated LXXLL SRC-1 peptide. The AlphaScreen signal increases when the complex receptor-coactivator is formed. The compound of this invention is a potent FXR agonists. Data are provided in Table 1.

Bile acids (BAs) modulate not only several nuclear hormone receptors, but are also agonists for the G protein-coupled receptor (GPCR) TGR5 (Makishima, et al., Science, 1999, 284, 1362-1365; Parks, et al., Science, 1999, 284, 1365-1368; Maruyama, et al., Biochem Biophys Res Commun, 2002, 298, 714-719; and Kawamata, et al., J Biol Chem, 2003, 278, 9435-9440). Signaling via FXR and TGR5 modulates several metabolic pathways, regulating not only BA synthesis and enterohepatic recirculation, but also triglyceride, cholesterol, glucose, and energy homeostasis. To evaluate the capacity of Compound 1 to activate TGR5, this compound and other comparison compounds were screened for an increase of intracellular cAMP as a read-out for TGR5 activation. Human enteroendocrine NCI-H716 cells constitutively expressing TGR5 were exposed to increasing concentrations of a compound of the invention, and intracellular cAMP levels were measured by TR-FRET. Lithocholic acid (LCA) was used as positive control. The compound of this invention shows high selectivity for FXR over TGR5. Data are provided in Table 1.

TABLE 1

| | FXR/TGR5 Activity | |
| --- | --- | --- |
| Compound | AlphaScreen Assay Human FXR Ref. CDCA = 15 ± 3 µM | HTR-FRET (cAMP) Human TGR5 (NCI-H716 cells) Ref. LCA = 7 ± 3 µM |
| Compound 1 | 0.14 ± 0.04 | >200 |
| Compound A | 0.2 ± 0.018 | 15 ± 5 |
| Compound B | 0.03 | 0.63 |
| Compound C | 175 | 0.9 |
| Compound F | 0.15 ± 0.05 | >200 |

TABLE 2

Compound 1 FXR Cross Species Activity

| hFXR EC$_{50}$(μM) | mFXR EC$_{50}$(μM) | rFXR EC$_{50}$(μM) | dFXR EC$_{50}$(μM) |
|---|---|---|---|
| 0.14 ± 0.04 | 0.6 ± 0.02 | 0.49 ± 0.01 | 1.65 ± 0.05 |

TABLE 3

Compound 1 TGR5 Cross Species Activity

| hTGR5 EC$_{50}$(μM) | mTGR5 EC$_{50}$(μM) | rTGR5 EC$_{50}$(μM) | dTGR5 EC$_{50}$(μM) |
|---|---|---|---|
| >200 | >200 | >200 | >200 |

Example 3. Nuclear Receptor Selectivity Profile

Using the AlphaScreen assay, the selectivity of Compound 1 against the following nuclear receptors involved in the metabolic pathways can be evaluated: LXRα, LXRβ, PXR, CAR, PPARα, PPARδ, PPARγ, RAR, RARα, VDR, TR, PR, RXRα, GR, and ER.

TABLE 4a

Nuclear Receptor Profile (agonist mode)

| | LXRα EC$_{50}$ (μM) | CAR EC$_{50}$ (μM) | LXRβ EC$_{50}$ (μM) | PPARα EC$_{50}$ (μM) | PPARδ EC$_{50}$ (μM) | PPARγ EC$_{50}$ (μM) | PXR EC$_{50}$ (μM) |
|---|---|---|---|---|---|---|---|
| Reference Compound | TO91317 0.12 | CITCO 0.005 | TO91317 0.06 | GW7647 0.003 | GW0742 0.004 | GW1929 0.012 | SR-12183 0.06 |
| Compound 1 | >300 | >300 | >300 | >300 | >300 | >300 | >300 |

TABLE 4b

Nuclear Receptor Profile (agonist mode)

| | RAR EC$_{50}$ (μM) | RXRα EC$_{50}$ (μM) | VDR EC$_{50}$ (μM) | ER EC$_{50}$ (μM) | GR EC$_{50}$ (μM) | PR EC$_{50}$ (μM) | TR EC$_{50}$ (μM) |
|---|---|---|---|---|---|---|---|
| Reference Compound | ATRA 0.001 | 9cisRA 0.004 | Dihydroxy VitD3 0.0001 | Estradiol 0.001 | Budenoside 0.002 | Progesterone 0.050 | T3 0.0001 |
| Compound 1 | >300 | >300 | >300 | >300 | >300 | >300 | >300 |

Example 4. FXR Target Gene Panel

To evaluate the capacity of Compound 1 to modulate FXR target genes, quantitative RT-PCR assays are performed (see FIG. 1). HepG2 cells are selected as a relevant cell line to determine whether a compound of the invention can regulate the endogenous FXR genetic network. The ability of a compound of the invention to induce FXR target genes is assessed by isolating total RNA from cells treated overnight with 1 μM of comparative compounds and a compound of the invention. Compound A is established as a potent FXR selective agonist and compound B is established as a dual potent FXR/TGR5 agonist.

FXR regulates the expression of several target genes involved in BA homeostasis. Briefly, FXR plays a central role in several metabolic pathways, including i.e., lipid metabolism, bile-acids metabolism, and carbohydrate metabolism. Regarding gene expression profiling, the genes encoding proteins involved in lipid metabolism include, e.g., APOCII, APOE, APOAI, SREBP-1C, VLDL-R, PLTP, and LPL; the genes encoding proteins involved in bile-acids metabolism include, e.g., OSTβ/β, BSEP, MRP2, SHP, CYP7A1, FGF19, SULT2A1, and UGT2B4; and the genes encoding proteins involved in carbohydrate metabolism include, e.g., PGC 1-alpha, PEPCK, and GLUT2.

Example 5. In Vitro Cytotoxicity

To evaluate in vitro cytotoxicity of Compound 1, two different assay methods are employed. The assays evaluate cell viability by measuring ATP levels and cytotoxicity by measuring LDH release. Adenosine Triphosphate (ATP) nucleotide represents the source of energy at the basic molecular level, as it is a multifunctional molecule that is used in every cell as a coenzyme and is an integral part of the mitochondrial DNA (Kangas, et al., Medical Biology, 1984, 62, 338-343; Crouch, et al., J Immunol. Methods, 1993, 160, 81-88; and Petty, et al., J Biolumin. Chemilumin. 1995, 10, 29-34). It has been called the "molecular unit of currency" when it comes to intracellular energy transfer. This is to ensure the important role of ATP in metabolism and a drop in ATP content is the first step in revealing cellular damage (Storer, et al., Mutation Research, 1996, 368, 59-101; and Cree and Andreotti, Toxicology In Vitro, 1997, 11, 553-556). Cell viability is determined as a measure of intracellular ATP related to the time of exposure and concentration of the test compounds (Sussman, Promega Cell Notes, Issue 3, 2002).

Another method to determine the viability of cells is to detect the integrity of the membrane that defines the cellular compartmentalization. Measuring the leakage of components out of the cytoplasm, in damaged cell membranes, indicates loss of membrane integrity, and LDH release is the method used to determine common toxicity in cells. HepG2 cells are treated with a compound of the invention, and serial dilutions are performed. LCA dilutions are added to the plated cells as assay controls together with no-cell and untreated cells. The assay is performed in triplicate for each test compound concentration.

TABLE 5

Compound 1 in vitro Cytotoxicity

| LDH<br>$EC_{50}$ (μM)<br>Ref Tamoxifen $EC_{50}$<br>35 ± 4 μM | ATP Content<br>$EC_{50}$ (μM)<br>Ref Tamoxifen $EC_{50}$<br>49 ± 9 μM |
|---|---|
| >300 | >300 |

Example 6. CYP450 Screening

To evaluate the potential of Compound 1 for drug-drug interactions, the six main CYP450 isoforms (CYP1A2, CYP2C9, CYP2C19, CYP2D6, CYP2E1, CYP3A4) are investigated (Obach, et al., J Pharmacol. Exp. Ther, 2006, 316, 336-348).

To determine interaction between Compound 1 and cytochrome P450 enzymes, the compound of the invention is analyzed by its capacity to inhibit (or not) the production of a fluorescent signal, using recombinant CYP450 proteins (baculosomes; Invitrogen), substrates and inhibitors (Bidstrup, et al., Br J Clin, Pharmacol, 2003, 56, 305-14). As a positive control, a selective inhibitor for each CYP450 isoform is tested in the same plate.

TABLE 6

CYP450 Screening

| CYP450 | Compound 1<br>$IC_{50}$ (μM) |
|---|---|
| CYP1A2 | >10 |
| Reference: Furafylline = 0.5 μM | |
| CYP3A4 (Green Substrate) | >10 |
| Reference: Ketoconazole = 0.044 μM | |
| CYP3A4 (Blue Substrate) | >10 |
| Reference: Ketoconazole = 0.04 μM | |
| CYP2C9 | >10 |
| Reference: Sulfaphenazole = 0.4 μM | |
| CYP2C19 | >10 |
| Reference: Miconazole = 0.06 μM | |
| CYP2D6 | >10 |
| Reference: Quinidine = 0.01 μM | |
| CYP2E1 | >10 |
| Reference: DCC = 0.4 μM | |

Example 7. Human ERG Potassium Channel

To determine ion channel function, the Predictor™ hERG Fluorescence Polarization assay is employed as it provides an efficient method for an initial determination of the propensity of test compounds to block the hERG channel (Dorn, et al. J Biomol. Screen, 2005, 10, 339-347). The assay is based on the assumption that the hERG potassium channel activity contributes to the resting membrane potential in permanently transfected cells, and thus a block of hERG channels should result in a depolarization of the cell membrane. The assay is designed to identify potential hERG channel blockers by producing data that accurately correlates with patch-clamp electrophysiology studies. Results from the Predictor™ assay demonstrate a high correlation with those obtained from patch clamp techniques (Dorn, et al. J Biomol Screen, 2005, 10, 339-347).

Membrane preparations from Chinese hamster ovary cells stably transfected with hERG potassium channel are used to evaluate the potential inhibitory effect of a compound of the invention on this channel using the Predictor™ fluorescence polarization assay. Reduction of membrane polarization as a result of inhibition of the hERG potassium channel is directly correlated with a reduction of the fluorescence polarization (FP).

The assay is performed in triplicate by using a 16-point dose-response of test compound and the positive controls E-4031 and Tamoxifen. An $IC_{50}$ of 15 nM (AmP=163) for E-4031 and 1.4 μM (ΔηтР=183) for Tamoxifen are obtained. An assay window more than 100 mP (millipolarization) is considered good. The non-linear regression curves are obtained by GraphPad Prism (Graph Pad Software Inc.) analysis, to calculate the $IC_{50}$ values.

TABLE 7

Compound 1 hERG Potassium channel activity
hERG inhibition
$IC_{50}$ (μM)

| |
|---|
| >100 |

Example 8. Pgp ATPase Activity

The impact of Compound 1 on Pgp ATPase activity was examined in Pgp-Glo™ Assay (Technical Bulletin; Pgp-Glo™ Assay Systems Instructions for Use of Products V3591 and V3601; Revised November 2015) according to the manufacturer's standard protocol.

TABLE 8

Compound 1 as Pgp Substrate
Pgp Substrate
$EC_{50}$ (μM)

| |
|---|
| >300 |

Example 9. Physiochemical Properties

Physiochemical properties of Compound 1 such as water solubility, critical micellar concentration, surface tension, and Log $P_A$ were determined using methods known in the art. Data are provided in Table 9.

TABLE 9

Physiochemical Properties

| | Ws [a]<br>(mM) | CMC [b]<br>(mM) | $ST_{CMC}$ [c] | $LogP_{A-}$ [d] |
|---|---|---|---|---|
| Compound 1 | | 2.0 | | 1.8 |
| Compound A | 9 | 2.9 | 43.2-48.8 | 2.5 |
| Compound B | hs | 1.3 | 43.3-47.9 | 2.0 |
| Compound C | 99 | 2 | 50.1 | 1.4 |
| Compound D | 15 | — | — | 2.9 |
| Compound E | 120 | 5.9 | 52.4 | 1.6 |
| Compound F | 143-150 | 15.8 | 47.8 | 0.8 |

[a] Ws: water solubility refers to BA as protonated species and therefore not evaluated for Compound B, TCDCA and TUDCA which are highly soluble (hs)
[b] CMC: Critical Micellar Concentration determined in 0.15M NaCl water solution
[c] $ST_{cmc}$: Surface Tension at CMC in 0.15M NaCl water solution
[d] $LogP_{A-}$: 1-octanol-water partition coefficient of the studied bile acids as ionized species

Example 10. Biliary Secretion and Metabolism of Compound 1 in Bile-Fistula Rat Aim and Rationale: The structural modification of a compound affects its hepatic uptake, hepatic transports, and secretion and intestinal absorption. Therefore, the knowledge of the biliary secretion after either iv or id administration together their metabolism is a key point in the candidate selection for additional studies. To evaluate the mode and efficiency of the intestinal absorption, Compound 1 is administered both intravenously (femoral infusion) and orally (duodenal infusion) at the same dose and its biliary secretion rate is evaluated in the bile fistula rat model. The choleretic effect on bile production is also evaluated. The differences in the area under the curve (AUC) of the biliary secretion vs time between iv and id administration account of its intestinal absorption and provide information about its bioavailability. Moreover, the hepatic and intestinal metabolism could also be quite different and therefore the biliary secretion of Compound 1 and its main (intestinal) and hepatic metabolites are determined.

Choleretic Effect—Duodenal Infusion

The bile fistula rat model is developed at the University of Bologna Lab facilities. Compound 1 is administered at a dose of about 1 μmol/kg/min (1 hour infusion) to a rat group via duodenal infusion (id). The rats have a bile fistula to collect bile samples at different times before and during the infusion. For duodenal infusion experiment, rats (250±10 g) are treated. Bile samples are collected every 15 minutes for four hours. In addition, 3 control rats are treated with saline solution under the same conditions for times and sampling (duodenal control rats).

Choleretic Effect—Intravenous Infusion

For the femoral infusion experiment, rats are treated with Compound 1 at about 1 μmol/min/kg. Femoral infusion starts after about 75 minutes of steady state and continues for about 60 min. Bile samples are collected about every 15 minutes for four hours. In addition, rats are treated with saline solution under the same conditions for times and sampling (femoral control rats).

The invention claimed is:

1. A compound of structure:

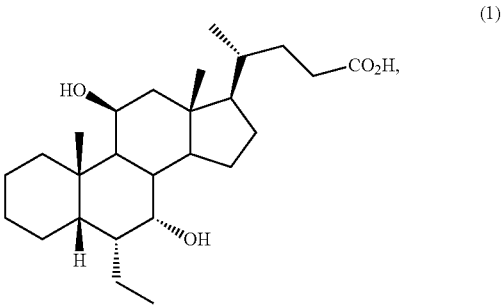 [SMILES: CC[C@H]1[C@@H](O)C2C3CC[C@H]([C@H](C)CCC(=O)O)[C@@]3(C)C[C@H](O)C2[C@@]2(C)CCCC[C@@H]12]

(1)

or a pharmaceutically acceptable salt or amino acid conjugate thereof.

2. The free acid of the compound of claim 1.

3. The pharmaceutically acceptable salt of the compound of claim 1.

4. A pharmaceutical composition comprising the compound of claim 1 and a pharmaceutically acceptable carrier or excipient.

* * * * *